United States Patent [19]

Maerkl et al.

[11] Patent Number: 4,740,525

[45] Date of Patent: Apr. 26, 1988

[54] PREPARATION OF ETHYLENE GLYCOL

[75] Inventors: Robert Maerkl, Fussgoenheim; Werner Bertleff, Viernheim; Wolfgang Harder, Weinheim; Rudolf Kummer, Frankenthal, all of Fed. Rep. of Germany

[73] Assignee: BASF Aktiengesellschaft, Ludwigshafen, Fed. Rep. of Germany

[21] Appl. No.: 900,770

[22] Filed: Aug. 26, 1986

[30] Foreign Application Priority Data

Sep. 14, 1985 [DE] Fed. Rep. of Germany ....... 3532877

[51] Int. Cl.$^4$ ..................... C07C 27/06; C07C 31/20
[52] U.S. Cl. .................................................. 518/701
[58] Field of Search ........................................ 518/701

[56] References Cited

U.S. PATENT DOCUMENTS 3,974,259  8/1976  Brown .
4,144,401  1/1979  Wall .
4,225,530  9/1980  Beisner et al. .
4,600,726  7/1986  Bertleff et al. ....................... 518/701

FOREIGN PATENT DOCUMENTS 33212    5/1981  European Pat. Off. .
55668    7/1982  European Pat. Off. .
85191    8/1983  European Pat. Off. .
2746245  4/1978  Fed. Rep. of Germany .

*Primary Examiner*—Howard T. Mars
*Attorney, Agent, or Firm*—John H. Shurtleff

[57] ABSTRACT

Ethylene glycol is prepared from carbon monoxide and hydrogen in homogeneous liquid phase under superatmospheric pressure and at elevated temperature in the presence of a rhodium-containing catalyst and in the presence of an organic solvent, the organic solvent used being a $C_2$–$C_{20}$-n-alkanol and the concentration of this alkanol, based on the total amount of the mixture, constantly being maintained at not less than 50% by weight.

11 Claims, No Drawings

PREPARATION OF ETHYLENE GLYCOL

The present invention relates to an improved process for preparing ethylene glycol from carbon monoxide and hydrogen in homogeneous liquid phase under superatmospheric pressure and at elevated temperature in the presence of a rhodium-containing catalysts and in the presence of an organic solvent.

This direct synthesis of lower alcohols from CO and $H_2$, where methanol and ethanol, inter alia, are formed in addition to the chief target product ethylene glycol, is, except for the improvement according to the invention, generally known from numerous publications. The solvents mentioned include alkanols such as methanol, ethanol, propanol, isobutanol and 2-ethylhexanol (see for example U.S. Pat. No. 3,974,259).

More recent patent publications such as EP-A-No. 0,085,191, by contrast, do not mention alkanols as solvents; on the contrary, it is expressly recommended there that the amount of ethylene glycol in the reaction mixture be kept below 20% by weight and the total concentration of ethylene glycol, methanol and ethanol be kept below 50% by weight.

We have found that the object of the present invention, namely to improve the above-defined direct synthesis for preparing in the main ethylene glycol, is achieved through obtaining considerably higher yields of ethylene glycol by ensuring that the reaction mixture constantly contains not less than 50% by weight, based on the total amount of the mixture, of a $C_2$–$C_{20}$-n-alkanol.

For economic reasons, preference is given to the $C_2$–$C_8$-alkanols, ie. ethanol, n-propanol, n-butanol, n-pentanol, n-hexanol, n-heptanol and n-octanol, and also to their mixtures, and of these, for process engineering reasons, to the sparingly water-soluble $C_5$–$C_8$-alkanols, since the low solubility in water makes it possible to isolate the synthesis products ethylene glycol, methanol and ethanol from the reaction mixture by a simple extraction with water.

Since the alkanols to be used according to the invention favor the direct synthesis of ethylene glycol, very high alkanol concentrations in the reaction mixture are in principle an advantage. However, since this would lead to uneconomically large volumes, an initial concentration of about 80–98% by weight is advisable. The reaction is then advantageously allowed to proceed until the end concentration, as a consequence of the newly formed ethylene glycol, is 50% by weight, preferably about 60–80% by weight. Further solvents such as those mentioned in EP-A-No. 0,085,191 for the purposes of the direct synthesis, can also be present, for example in order to increase the solubility of the catalyst. Some of these solvents such as open-chain and cyclic tetraalkylureas, lactones and also N-aryl- and N-alkyl-pyrrolidones and -imidazolidones, in particular N-methylpyrrolid-2-one, 1,5-dimethylpyrrolid-2-one and 1,3-dimethylimidazolid-2-one, have a favorable effect on the reaction and therefore are preferred.

The catalyst used is either rhodium alone or rhodium together with other carbonyl-forming metals such as ruthenium, palladium, platinum, iridium, iron, nickel and in particular cobalt, and in these cases the rhodium content should be at least 5 mol%.

Since the active carbonyl complexes form of their own accord during the reaction, the catalysts can be used in metallic form or preferably in the form of their salts or complex compounds such as the carbonyl complex or complexes with, for example, acetylacetone.

Particular preference is given according to earlier German Patent Application No. P 34 27 138.4 to cocatalysts or catalyst mixtures with rhodium and cobalt as active metals, in which the molar ratio of rhodium to cobalt is from about 20:1 to 60:1.

The rhodium concentration, or the total concentration of carbonyl-forming metals, in the reaction medium is in principle infinitely variable, since it essentially affects only the rate of reaction and hence the spacetime yield. Satisfactory space-time yields are generally obtained within a concentration range of 0.01–0.5% by weight of metal; higher concentrations do not lead to any further significant economic advantages, and at lower concentrations, for example down to 0.005% by weight, the reaction slows down accordingly.

As is common knowledge for the direct synthesis, it is also advisable in the present case to carry out the process in the presence of an open-chain or cyclic tertiary amine such as N-methylmor-pholine, since such compounds enter the catalysts as ligands and are known to increase their stability. The amount of these compounds is preferably about 1–50 moles per mol of the central atoms.

The total pressure is advantageously within the range of 300–3000, preferably 600–2000, bar, the partial pressure of the carbon monoxide being preferably 20–80%, in particular 30–60%, of the total pressure.

Good results are obtained at 180°–280° C., the range of 200°–240° C. being generally preferable.

The reaction can be carried out batchwise or continuously in a conventional manner. The reaction mixture is worked up either by distillation or, if a water-insoluble alkanol is used as the reaction medium, particularly advantageously by extracting with water and subsequently fractionating the extract phase.

The latter procedure has the advantage that the catalyst-containing raffinate phase left behind can be immediately reused for a further reaction batch, since the water passing into the raffinate phase does not interfere with the reaction. This procedure is, from a process engineering viewpoint, particularly highly suitable for continuous operation.

The workup by distillation alone, which is necessary when using water-soluble alkanols, gives a catalyst-containing bottom phase which can be likewise recycled into the reaction.

According to observations to date, the novel use of alkanols as reaction medium consistently gives a distinctly improved yield of ethylene glycol, compared with the procedure involving the use of lower alkanol concentrations or the use of other solvents, under otherwise identical reaction conditions. In other words, the other reaction conditions are immaterial with respect to the relative improvement.

EXAMPLE 150 g lots of a solution comprising
  1.0 g of $Rh(CO)_2 \times$ acetylacetone (=0.4 g of Rh)
  0.026 g $Co_2(CO)_8$ (=0.009 g of Co)
  1.88 g of N-methylmorpholine
  a g of 1,5-dimethylpyrrolid-2-one and
  b g of hexan-1-ol,
a+b amounting to around 200 g, were made to react with an equimolar $CO/H_2$ mixture for 5 hours at 230° C. and a total pressure of 1500 bar.

Details and results of these experiments are given in the table below. The yields were determined by gas chromatography.

| Exp. No. | a [g] | b [g] | Yield [g] of | | |
|---|---|---|---|---|---|
| | | | MeOH | EtOH | HO—$CH_2$—$CH_2$—OH |
| for comparison | | | | | |
| 1 | 200 | 0 | 15.8 | 2.2 | 37.2 |
| 2 | 140 | 60 | 13.9 | 2.4 | 39.6 |
| 3 | 110 | 90 | 6.4 | 14.5 | 35.2 |
| according to the invention | | | | | |
| 4 | 60 | 140 | 15.0 | 11.0 | 60.4 |
| 5 | 20 | 180 | 14.5 | 9.9 | 54.1 |

As can be seen the yield of ethylene glycol in experiments 4 and 5 is distinctly higher than in the comparative experiments.

We claim:

1. In a process for preparing ethylene glycol by reacting carbon monoxide and hydrogen in homogeneous liquid phase under superatmospheric pressure and at elevated temperature in the presence of a rhodium-containing catalyst and in the presence of an organic solvent, the improvement which comprises:

carrying out the reaction using a catalyst which is a rhodium/cobalt cocomplex or a mixture of a rhodium and a cobalt complex, the molar ratio of rhodium to cobalt ranging from about 20:1 to 60:1, and using an organic solvent which comprises a $C_2$–$C_{20}$-n-alkanol, the concentration of this alkanol, based on the total amount of the liquid phase reaction mixture, being constantly maintained at not less than 50% by weight.

2. A process as claimed in claim 1, wherein the alkanol concentration at the start of the reaction is 80–95% by weight.

3. A process as claimed in claim 1, wherein the alkanol is a $C_2$–$C_8$-alkanol.

4. A process as claimed in claim 1, wherein the alkanol is a $C_5$–$C_8$-alkanol.

5. A process as claimed in claim 1 wherein the alkanol is hexan-1-ol.

6. A process as claimed in claim 5 wherein the hexan-1-ol concentration at the start of the reaction is at least 70% by weight.

7. A process as claimed in claim 1 wherein the solvent comprises a mixture of said alkanol and a solvent which increases the solubility of the catalyst.

8. A process as claimed in claim 7 wherein the solvent other than the alkanol is selected from the group consisting of open-chain and cyclic tetraalkylureas, lactones, N-aryl- and N-alkyl-pyrrolidones, and N-aryl- and N-alkyl-imidazolidones.

9. A process as claimed in claim 7 wherein the solvent other than said alkanol is selected from the group consisting of N-methylpyrrolid-2-one, 1,5-dimethylpyrrolid-2-one, and 1,3-dimethylimidazolid-2-one.

10. A process as claimed in claim 1 wherein the stability of the catalyst is increased by carrying out the reaction in the presence of an open-chain or cyclic tertiary amine.

11. A process as claimed in claim 10 wherein the tertiary amine is N-methylmorpholine.

* * * * *